(12) United States Patent  
Fargahi

(10) Patent No.: US 11,185,431 B2  
(45) Date of Patent: Nov. 30, 2021

(54) PROCESS, CONFIGURATION AND APPARATUS FOR FIXING A STENT TO A BALLOON OF A BALLOON CATHETER

(71) Applicant: BIOTRONIK AG, Buelach (CH)

(72) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 127 days.

(21) Appl. No.: 16/512,980

(22) Filed: Jul. 16, 2019

(65) Prior Publication Data
US 2020/0069450 A1 Mar. 5, 2020

(30) Foreign Application Priority Data

Aug. 28, 2018 (DE) .......................... 102018120939.8

(51) Int. Cl.
| | |
|---|---|
| *A61F 2/95* | (2013.01) |
| *A61F 2/958* | (2013.01) |
| *B29C 49/20* | (2006.01) |
| *B29K 77/00* | (2006.01) |
| *B29L 31/00* | (2006.01) |

(52) U.S. Cl.
CPC .............. *A61F 2/958* (2013.01); *B29C 49/20* (2013.01); *A61F 2/9522* (2020.05); *A61F 2002/9583* (2013.01); *A61F 2240/001* (2013.01); *B29K 2077/00* (2013.01); *B29L 2031/7543* (2013.01)

(58) Field of Classification Search
CPC ... A61F 2/9522; Y10T 29/49; Y10T 29/49826
See application file for complete search history.

(56) References Cited

U.S. PATENT DOCUMENTS

| | | | | |
|---|---|---|---|---|
| 5,824,043 | A | * | 10/1998 | Cottone, Jr. .............. A61F 2/07 623/1.13 |
| 6,027,529 | A | | 2/2000 | Roychowdhury et al. |
| 6,063,092 | A | * | 5/2000 | Shin ........................ A61F 2/958 606/108 |
| 6,159,237 | A | | 12/2000 | Alt et al. |
| 6,666,880 | B1 | | 12/2003 | Chiu et al. |

(Continued)

FOREIGN PATENT DOCUMENTS

| | | |
|---|---|---|
| DE | 69837704 T2 | 9/2007 |
| DE | 102008006092 A1 | 7/2009 |
| EP | 1397090 B1 | 8/2010 |

OTHER PUBLICATIONS

English translation DE 69837704 (Year: 2007).*

*Primary Examiner* — Jason L Vaughan
*Assistant Examiner* — Amanda Kreiling
(74) *Attorney, Agent, or Firm* — Laurence A. Greenberg; Werner H. Stemer; Ralph E. Locher

(57) ABSTRACT

A process for fixing an implant to a balloon includes providing, in an interior of a sleeve, a heated balloon having a pressurizable balloon interior and an implant crimped to the balloon. The implant has a supporting structure with a multiplicity of through openings. A negative pressure is applied in the interior of the sleeve and a positive pressure is applied to the balloon interior, so that the balloon is deep-drawn into the openings of the implant, producing a form-locking connection between the balloon and the implant. A configuration for carrying out the process and an apparatus for fixing an implant to a balloon are also provided.

30 Claims, 2 Drawing Sheets

(56) References Cited

U.S. PATENT DOCUMENTS

| | | | | |
|---|---|---|---|---|
| 6,745,445 B2* | 6/2004 | Spilka | ................... | A61F 2/958 29/407.08 |
| 8,221,484 B2 | 7/2012 | Wesselmann | | |
| 2007/0006441 A1 | 1/2007 | McNiven et al. | | |
| 2013/0304179 A1* | 11/2013 | Bialas | .................. | A61M 25/09 623/1.11 |

* cited by examiner

PROCESS, CONFIGURATION AND APPARATUS FOR FIXING A STENT TO A BALLOON OF A BALLOON CATHETER

CROSS-REFERENCE TO RELATED APPLICATION

This application claims the priority, under 35 U.S.C. § 119, of German Patent Application DE 10 2018 120 939.8, filed Aug. 28, 2018; the prior application is herewith incorporated by reference in its entirety.

BACKGROUND OF THE INVENTION

Field of the Invention

The invention relates to a process, a configuration and an apparatus for fixing an implant to a balloon of a balloon catheter as well as a configuration with an implant fixed to a balloon. The invention is described by using an example of a stent and a balloon of a balloon catheter. However, in principle the invention is suitable for fixing any implant to a balloon. Such implants are, for example, stents, heart valve prostheses with a stent-shaped skeletal structure, occluders, or generally tubular, balloon-expandable implants.

When implants, especially stents, are crimped to balloons of a balloon catheter, it is very important that the implants be securely fixed to the respective balloon of a balloon catheter, so that they do not slip with respect to the balloon during implantation. Therefore, it is important to achieve a sufficient implant or stent dislodgement force. In the case of an implant or stent crimped to a balloon, the stent dislodgement force represents the sum of the form-locking and force-locking connections.

In the relevant standards (e.g., ASTM standard F2394-07), as well as in the framework of the present invention, crimping an implant/stent to a balloon is understood to mean securing the stent to the balloon by compressing the stent on the balloon in the radial direction (in the direction toward the folded balloon) so that the stent undergoes plastic deformation.

With regard to stent dislodgement force, form-locking connections are produced by at least two connection partners (in this case the stent and the balloon) interlocking. That means that the connection partners also cannot be detached without the transmission of power or if the transmission of power is interrupted. In other words, a form-locking connection involves the one connection partner being in the way of the other connection partner.

Force-locking connections presume a normal force on the surfaces to be connected with one another. Displacement of those surfaces with respect to one another is prevented as long as the counterforce caused by the static friction is not exceeded. The force-locking or frictional engagement is lost and the surfaces slide on one another if the load force acting in the tangential direction is greater than the force of static friction.

SUMMARY OF THE INVENTION

It is accordingly an object of the invention to provide a process, a configuration and an apparatus for fixing a stent to a balloon of a balloon catheter, which overcome the hereinafore-mentioned disadvantages of the heretofore-known processes configurations and apparatuses of this general type and which further improve the fixation of an implant that is crimped to a balloon with respect to the balloon to prevent the risk of the implant slipping, especially during an implantation.

With the foregoing and other objects in view there is provided, in accordance with the invention, a process for fixing an implant to a balloon (for a balloon catheter), the process comprising providing, in an evacuable interior of a sleeve, a (preferably heated) balloon and, crimped to this balloon, an implant that has a supporting structure with multiplicity of through openings, applying a negative pressure in the interior of the sleeve and applying a positive pressure to the balloon interior, so that the preferably heated balloon is deep-drawn into the openings of the implant, producing a form-locking connection between the balloon and the implant or the supporting structure of the implant. The heated balloon can be provided in the interior of the sleeve, e.g., by heating the balloon (e.g., by using a suitable heating device) outside the interior of the sleeve and then placing the heated balloon in the interior of the sleeve, or by placing the balloon in the interior of the sleeve and heating it in the interior of the sleeve (e.g., by using a heating device that is integrated into the sleeve or that is thermally connected with the sleeve).

The inventive process is especially suitable for fixing a stent to a balloon of a balloon catheter, in the framework of this application, a stent is understood to mean a permanent or degradable tubular structure that can be implanted into a body vessel, especially a blood vessel. The stent can also have one or more coatings, in particular coatings containing an active ingredient. Such stents advantageously have a multiplicity of struts, which form the structure of the stent and which have, for the most part, a meandering course and are disposed as a multiplicity of rings and/or helices and are connected together in such a way that they form a substantially cylindrical structure with a multiplicity of gaps or openings between the struts.

That is, the process involves, in particular, applying a negative pressure in the interior of the sleeve, applying a positive pressure to the balloon interior, and heating the balloon in such a way (in particular beforehand or in the interior of the sleeve), that the balloon forms a multiplicity of plastically deformed material areas, each of which projects into or interlocks with an associated opening in the implant structure in a form-locking manner, producing the form-locking connection between the balloon and the implant.

Thus, this inventive negative pressure or vacuum deep drawing produces a high degree of deformation, and thus an optimal form-locking connection between the implant and the balloon. This advantageously leads to an increased implant dislodgement force.

The openings through the implant or stent are also referred to as cells of the implant. Each cell or opening through the implant is bounded by the respective supporting structure of the implant, which can be formed, e.g., by a multiplicity of struts that are connected with one another. The struts can be in a single piece or integrally connected with one another. In particular, the supporting structure can form a grid structure. Such an implant can be formed, e.g., by corresponding working of a tubular (preferably metallic) preform, this working involving cutting, e.g., by using lasers, the cells or openings through the implant, producing the supporting structure or struts with the cells (openings). However, it is also conceivable to produce the supporting structure of the implant or the cells/opening through the implant in another way.

One embodiment of the inventive process provides the implant in the interior of the sleeve being surrounded by a tube disposed in the interior, this tube having a circumferential wall surrounding the implant and the balloon. I.e., the implant lies between the (pressurized) balloon and the tube.

One embodiment of the inventive process further provides that the tube has at least one opening that is formed through the wall of the tube.

One embodiment of the inventive process further provides that the tube has a multiplicity of openings that are disposed through the wall of the tube. These individual openings can be disposed equidistant to one another.

One embodiment of the invention further provides that the tube is made of a metal, especially a stainless steel.

One embodiment of the inventive process further provides that the tube has an inside diameter that corresponds to an outside diameter of the implant fixed to the balloon.

In particular, the multiplicity of openings through the tube form perforations of the tube. The at least one or the multiplicity of openings through the tube, which serve, in particular, as nozzle openings for better distribution of the negative pressure in the interior of the sleeve, can be made in the tube, e.g., by using a laser.

One embodiment of the invention further provides that the respective opening through the tube is circular and has a diameter that lies in the range from 0.05 mm to 01 mm.

One embodiment of the inventive process allows the openings through the tube to be in the form of slits.

One embodiment of the inventive process further provides that the pressure in the balloon interior lies in the range from 10 bar to 30 bar. The pressure especially lies in the range from 10 bar to 20 bar, especially in the range from 13 bar to 17 bar, especially 15 bar.

One embodiment of the inventive process further provides that the negative pressure in the interior of the sleeve is less than or equal to 0.6 bar, especially in the range from 0.01 bar to 0.6 bar, especially in the range from 0.1 bar to 0.6 bar, especially in the range from 0.3 bar to 0.6 bar.

One embodiment of the inventive process further provides that the heating of the balloon involves it being heated to a final temperature that allows the balloon to undergo plastic deformation at the pressure and the negative pressure.

One embodiment of the inventive process further provides that he final temperature lies in one of the following ranges:
  in the range from 40° C. to 150° C.;
  in the range from 40° C. to 140° C. (especially in the case when the balloon is formed of PA 12, see below),
  in the range from 60° C. to 150° C. (especially in the case when the balloon is formed of Pebax® 7033, see below),
  in the range from 50° C. to 110° C.;
  in the range from 100° C. to 110° C., especially 102° C. to 107° C. (especially in the case when the material of the balloon is Pebax® 7033 and/or in the case of a metallic implant or stent, especially one that has no medication applied to it);
  in the range from 50° C. to 60° C., especially 53° C. to 57° C. (especially in the case when the balloon material is PA 12 and/or when the implant or stent has a medication applied to it, i.e., when it s a so-called drug eluting stent (DES), i.e., a stent that is configured to release a medication, in contrast to an uncoated stent (BMS)).

One embodiment of the inventive process further provides for the balloon being made of a balloon material that has a glass-transition temperature, the final temperature being greater than or equal to the glass-transition temperature, in particular the final temperature deviating from the glass-transition temperature by no more than 10%, especially no more than 5%, especially no more than 1%. The glass-transition temperature can be determined by using a method known to the person skilled in the art, such as, for example, thermoanalytical methods (DSC, DMA, DIL, LFA).

That is, in other words, the balloon is specially heated so that it can undergo plastic deformation, the balloon coming to lie true to the contour of and tightly against the implant during the deep drawing produced by the positive pressure in the balloon interior and the negative pressure in the interior of the sleeve.

According to one embodiment of this invention, the balloon is formed of a material such as, e.g., polyamide or modifications of it, such as, e.g., a polyether block amide (e.g., Pebax®). The material can also be a thermoplastic elastomer, e.g., TPE-A. These semi-crystalline plastics (many common plastics have a crystalline component from 10% to 80%) possess both a glass-transition temperature below which the amorphous phase freezes (accompanied by embrittlement) and also a melting point at which the crystalline phase melts. The melting point clearly separates the rubber-elastic range from the flow range.

According to one embodiment of this invention, the balloon can, in particular, be made from, or formed of one of the following materials: a polyamide, especially PA 12, e.g., Grilamid® L25 polyamide 12; a polyether block amide (PEBA), e.g., Pebax® 3533 or Pebax® 7033; PET; PEEK; TPU.

In particular, Grilamid® L25 polyamide 12 is a semi-crystalline thermoplast with a glass-transition temperature of 37° C. and with a melting point of 178° C. Peba or PEBAX® 3533 (CAS no. 77402-38-1) or PEBAX® 7033 (CAS no. 77402-38-1) are semi-crystalline thermoplastic elastomers (TPE), PEBAX® 3533 having, e.g., a glass-transition temperature of −65° C. and a melting point of 144° C. Furthermore, PET (polyethylene terephthalate) can have, e.g., a glass-transition temperature of 70° C. and a melting point of, e.g., 255° C. In particular, PEEK (polyetheretherketone) is also a semi-crystalline thermoplast with a glass-transition temperature of, e.g., 143° C. and with a melting point of, e.g., 340° C. Furthermore, in the framework of this invention thermoplastic polyurethane (TPU) can be used as a material for the balloon.

One embodiment of the inventive process further provides for the balloon to be exposed to the final temperature when the balloon interior has positive pressure applied to it and the interior of the sleeve has negative pressure applied to it, and for this be done over a time period of at least 10 seconds, especially at least 20 seconds, especially at least 30 seconds, especially at least 40 seconds, especially at least 50 seconds, especially at least 60 seconds.

One embodiment of the process provides for the balloon to be exposed to the final temperature when the balloon interior has positive pressure applied to it and the interior of the sleeve has negative pressure applied to it, and for this to be done over a time period of at least 10 seconds to 100 seconds, especially 20 seconds to 80 seconds, especially 30 seconds to 60 seconds, especially 20 seconds to 40 seconds, especially 25 seconds to 35 seconds, especially 50 seconds to 70 seconds, especially 55 seconds to 65 seconds.

The time periods 20 seconds to 40 seconds and 25 seconds to 35 seconds, are used especially when the implant is a stent that is configured to release a medication (DES). In this case, the balloon can be formed, e.g., of PA 12 or another polyamide.

The time periods 50 seconds to 70 seconds and 55 seconds to 65 seconds are used especially when the implant is a pure metal stent (BMS). In this case, the balloon can be formed, e.g., of PEBAX® 7033 or another TPE, especially TPE-A.

With regard to the different stent configurations (DES or BMS), the invention can be carried out especially with the following sample parameters:

| Stent | Balloon material | Final temperature °(C) | Time period or process duration (seconds) | Pressure in balloon interior (bar) |
|---|---|---|---|---|
| BMS | PEBAX ® 7033 | 105 ± 3 | 60 | 15 ± 0.5 |
| DES | PA 12 | 55 ± 2 | 30 | 15 ± 0.5 |

One embodiment of the inventive process further provides for the balloon to be heated by using Joule heat, in particular by using an electrical conductor. Furthermore, when the balloon is being heated it is preferably located in the interior of the sleeve and is, in particular surrounded by the tube. The electrical conductor can be disposed on the sleeve or embedded in it. However, the balloon along with the implant crimped to it can also be heated outside the sleeve (see above).

One embodiment of the inventive process further provides for positive pressure to be applied to the balloon interior before the balloon is heated, and/or for the negative pressure to be applied to the interior of the sleeve before the balloon is heated. This applies especially in the case when the balloon is heated in the interior of the sleeve.

However, it is also conceivable to apply the negative pressure at the same time as the balloon is heated, or only after the balloon is heated to the final temperature in the interior.

It is also conceivable to apply positive pressure to the balloon interior at the same time as the balloon is heated, or only after the balloon is heated to the final temperature.

With the objects of the invention in view, there is also provided a configuration having an implant, especially a stent, that is crimped to a balloon, the implant being fixed to the balloon by using the inventive process.

With the objects of the invention in view, there is furthermore provided an apparatus for fixing an implant, especially a stent, to a balloon, the apparatus being used, in particular, in the inventive process.

The inventive apparatus has at least the following:
a sleeve that has an interior to hold an implant that is crimped to a balloon;
a pump that can be brought in flow connection with the interior and that is configured to produce a negative pressure in the interior of the sleeve;
a device that can be brought in flow connection with a balloon interior of the balloon and that is configured to apply a positive pressure to the balloon interior of the balloon; and
a heating device that is configured to heat he balloon, especially if the balloon is disposed in the interior of the sleeve (or if the balloon is disposed outside the interior of the sleeve or before the balloon is disposed in the interior of the sleeve).

One embodiment of the inventive apparatus provides for the device to have a tube that is configured to surround the implant if the implant is disposed in the interior of the sleeve, so that the implant is disposed between the balloon and the tube.

One embodiment of the inventive apparatus further provides for the tube to have at least one through opening or a multiplicity of through openings, with the respective through opening being formed in a circumferential wall of the tube.

Regarding other features of the tube of the apparatus, reference is made to the features of the tube already described above.

One embodiment of the inventive apparatus further provides for the sleeve of the device to be formed by a rigid mold, with the sleeve having a hermetically sealable opening through which the balloon along with the implant can be disposed in the interior of the sleeve, with it being possible to bring a pipe communicating with the balloon interior out of the sleeve through a hermetically sealable feedthrough of the sleeve. The device for producing the positive pressure in the balloon interior is preferably configured to be put in flow connection with this pipe to apply pressure to the balloon interior. The pipe can be a lumen of a catheter connected with the balloon.

Other features which are considered as characteristic for the invention are set forth in the appended claims.

Although the invention is illustrated and described herein as embodied in a process, a configuration and an apparatus for fixing a stent to a balloon of a balloon catheter, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
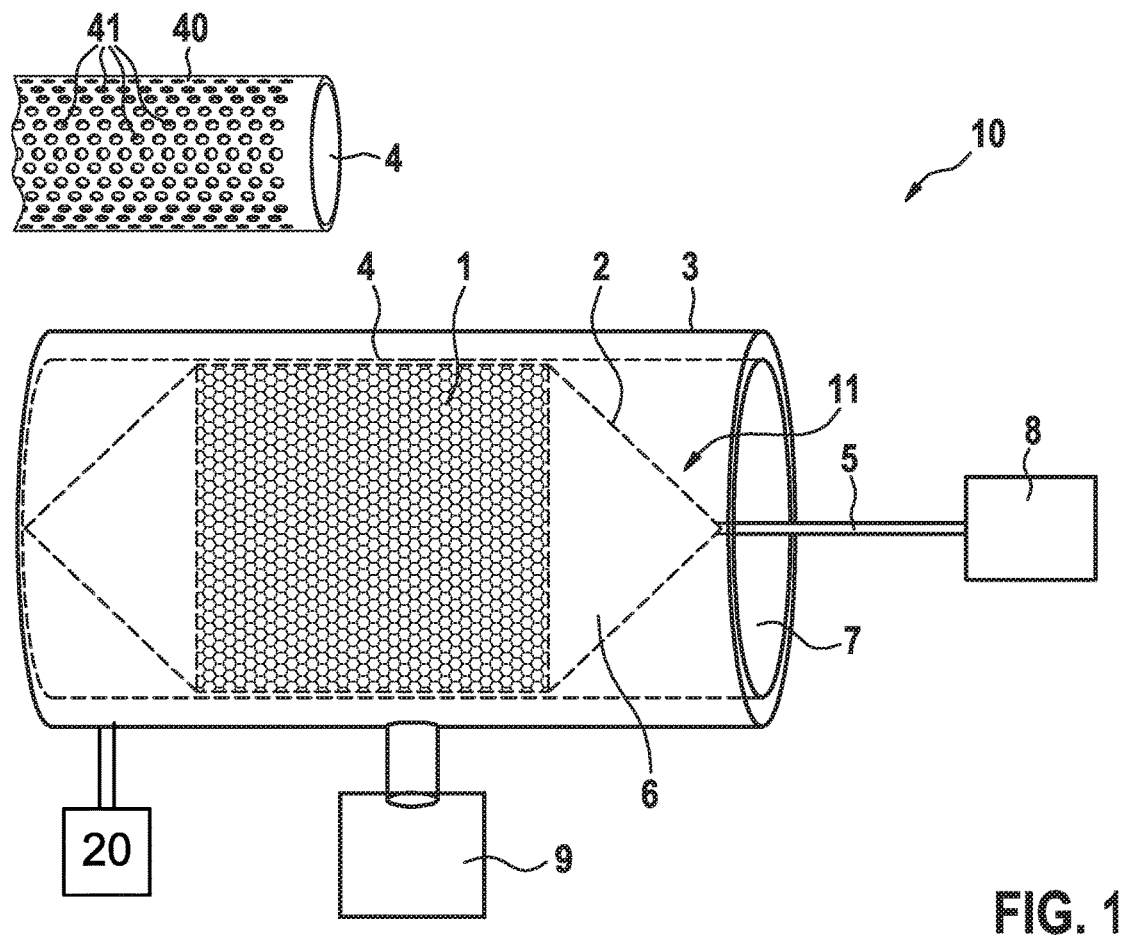
FIG. 1 is a diagrammatic, perspective view of an apparatus that can be used to carry out the inventive process.
Figure 2:
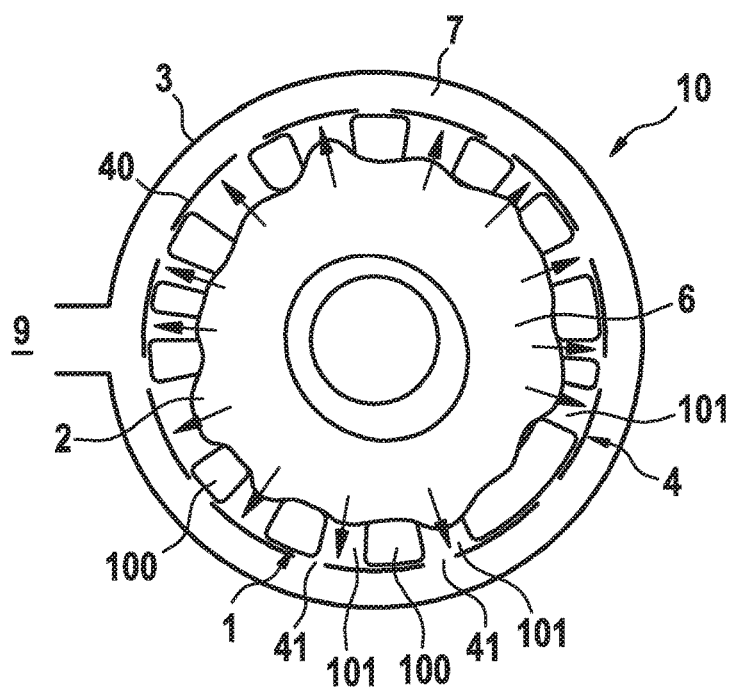
FIG. 2 is a cross-sectional view through a stent that is crimped on a balloon and that is disposed in the apparatus according to FIG. 1.

Referring now in detail to FIG. 1 in connection with FIG. 2, there is seen an apparatus 10 that is configured to carry out the inventive process. In the process, a heated balloon material of a balloon 2 is deep drawn into openings 101 through a stent 1 under pressure in a balloon interior 6 with the help of a negative pressure (especially a vacuum) applied from outside, with each of these openings 101 being bordered by a supporting structure 100 of the stent 1 (also see FIG. 2).

Figure 1A:
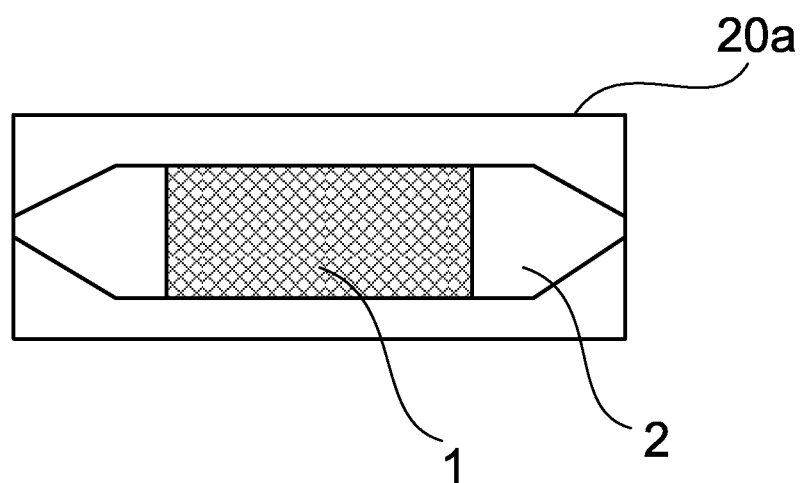
FIG. 1A is an elevational view of an alternative embodiment of the invention.

The apparatus 10 has a mold or sleeve 3 that can be heated by using a heating device 20. The sleeve 3 can be heated by using electrical heating elements or inductively. However, as shown in FIG. 1A, alternatively or additionally, the balloon 2 can also be heated, by using a separate heating device 20a, to the necessary final temperature outside of the sleeve 3 and can then be disposed in an interior 7 of the sleeve 3.

Furthermore, the sleeve 3 is connected to a pump 9 to produce a negative pressure in the interior 7 of the sleeve 3. The interior 7 of the sleeve 3 preferably has disposed in it a perforated tube 4, having an inside diameter which corresponds, in particular, to the final diameter of the stent 1 crimped to the balloon 2. According to one embodiment, the perforation of the tube 4 is formed by a multiplicity of openings 41 or nozzle bores 41 through the tube 4, which are cut in a wall 40 of the tube 4, e.g., with the help of a laser. The diameter of these holes 41 can be, e.g., 0.05 mm to 0.1 mm. Alternatively, the tube 4 that is used can have slits instead of holes. The material of the tube 4 can be formed of stainless steel. In order to apply a pressure to the balloon interior 6, a pipe 5 that is in flow connection with the balloon 2 is brought out of the sleeve 3 or the mold 3, with a device 8 to produce the pressure being connected with this pipe 5. The pipe can be a lumen of a catheter connected with the balloon 2.

The stent 1 is disposed between the folded balloon 2 and the perforated tube 4 (see especially FIG. 2). For deep drawing of the heated balloon 2, the pressure is now applied to the balloon interior 6, while the interior 7 of the sleeve 3 is evacuated, so that the negative pressure is applied there. The pressure in the balloon interior 6 is, for example, 15 bar and the negative pressure in the interior 7 of the sleeve 3 is, for example, in the range from about 0.3 bar to 0.6 bar. For deep drawing (caused by the pressure and the negative pressure), the balloon 2 with the stent 1 crimped on it can be heated by using the heating device (e.g., in the form of a heating coil) 20 to a final temperature (e.g., above the glass-transition temperature of the balloon material and below the melting point), so that it can undergo plastic deformation. In the case of pure metal stents (BMS), this final temperature can be, e.g., 105° C. and for so-called DES (drug eluting stents) it can be, for example, 55° C. In order to accomplish this, reference is made to the above-described embodiments and examples. During the deep drawing which is, in particular, performed over a predefined period of time (e.g., 30 s in the case of DES or 60 s in the case of BMS; also see above), the balloon 2 now comes to lie true to the contour of and tightly against the stent 1, as is indicated in FIG. 2 using arrows, with individual areas of the material of the stent 1 undergoing plastic deformation and, as they do so, penetrating into the cells 101 or openings 101 through the stent 1, and each of them therefore achieving a form-locking connection there with the supporting structure 100 of the stent 1.

Thus, as a result, the inventive solution produces an optimal form-locking connection between the stent 1 and the balloon 2, which increases the stent dislodgement force. This advantageously reduces the risk of stent displacement and the risk of stent dislodgment from the balloon (see ASTM F2394-07).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A process for fixing an implant to a balloon, the process comprising the following steps:
   providing a balloon in an interior of a sleeve;
   crimping to the balloon an implant having a supporting structure with a multiplicity of through openings;
   applying a negative pressure to the interior of the sleeve while applying a positive pressure to an interior of the balloon, causing the balloon to be deep-drawn into the through openings of the implant and producing a form-locking connection between the balloon and the supporting structure of the implant.

2. The process according to claim 1, which further comprises heating the balloon in the interior of the sleeve.

3. The process according to claim 2, which further comprises carrying out the heating of the balloon by heating the balloon to a final temperature.

4. The process according to claim 3, which further comprises selecting the final temperature to be in one of the following ranges:
   from 40° C. to 150° C.;
   from 40° C. to 140° C. when the balloon is formed of PA 12;
   from 60° C. to 150° C. when the balloon is formed of PEBAX® 7033;
   from 50° C. to 110° C.;
   from 100° C. to 110° C. or from 102° C. to 107° C. when the material of the balloon is PEBAX® 7033;
   from 50° C. to 60° C. or from 53° C. to 57° C. when a material of the balloon is PA 12.

5. The process according to claim 3, which further comprises making the balloon from a balloon material having a glass-transition temperature, and selecting the final temperature to be greater than or equal to the glass-transition temperature.

6. The process according to claim 5, which further comprises selecting the final temperature as deviating from the glass-transition temperature by no more than 10%.

7. The process according to claim 5, which further comprises selecting the final temperature as deviating from the glass-transition temperature by no more than 5%.

8. The process according to claim 5, which further comprises selecting the final temperature as deviating from the glass-transition temperature by no more than 1%.

9. The process according to claim 3, which further comprises exposing the balloon to the final temperature when the balloon interior has the positive pressure applied to it and the interior of the sleeve has the negative pressure applied to it, and exposing the balloon to the final temperature over a time period of 10 seconds to 100 seconds.

10. The process according to claim 3, which further comprises exposing the balloon to the final temperature when the balloon interior has the positive pressure applied to it and the interior of the sleeve has the negative pressure applied to it, and exposing the balloon to the final temperature over a time period of 20 seconds to 80 seconds.

11. The process according to claim 3, which further comprises exposing the balloon to the final temperature when the balloon interior has the positive pressure applied to it and the interior of the sleeve has the negative pressure applied to it, and exposing the balloon to the final temperature over a time period of 30 seconds to 60 seconds.

12. The process according to claim 3, which further comprises exposing the balloon to the final temperature when the balloon interior has the positive pressure applied to it and the interior of the sleeve has the negative pressure applied to it, and exposing the balloon to the final temperature over a time period of 20 seconds to 40 seconds.

13. The process according to claim 3, which further comprises exposing the balloon to the final temperature when the balloon interior has the positive pressure applied to it and the interior of the sleeve has the negative pressure applied to it, and exposing the balloon to the final temperature over a time period of 25 seconds to 35 seconds.

14. The process according to claim 3, which further comprises exposing the balloon to the final temperature when the balloon interior has the positive pressure applied to it and the interior of the sleeve has the negative pressure applied to it, and exposing the balloon to the final temperature over a time period of 50 seconds to 70 seconds.

15. The process according to claim 3, which further comprises exposing the balloon to the final temperature when the balloon interior has the positive pressure applied to it and the interior of the sleeve has the negative pressure applied to it, and exposing the balloon to the final temperature over a time period of 55 seconds to 65 seconds.

16. The process according to claim 2, which further comprises applying pressure as at least one of:
   positive pressure applied to the balloon interior before the balloon is heated, or
   negative pressure applied to the interior of the sleeve before the balloon is heated.

17. The process according to claim 1, which further comprises heating the balloon in the interior of the sleeve by:
   heating the balloon outside the interior of the sleeve and then placing the heated balloon along with the implant in the interior of the sleeve, or
   placing the balloon along with the implant in the interior of the sleeve and heating the balloon in the interior of the sleeve.

18. The process according to claim 1, which further comprises providing a tube having a circumferential wall, placing the tube in the interior of the sleeve, surrounding the implant in the interior of the sleeve with the tube, and surrounding the implant and the balloon with the circumferential wall of the tube.

19. The process according to claim 18, which further comprises providing the tube with at least one through opening formed in the wall of the tube.

20. The process according to claim 18, which further comprises providing the tube with a multiplicity of through openings disposed in the wall of the tube.

21. The process according to claim 1, which further comprises applying the positive pressure in the balloon interior in a range from 10 bar to 30 bar.

22. The process according to claim 1, which further comprises applying the positive pressure in the balloon interior in a range from 14.5 bar to 15.5 bar.

23. The process according to claim 1, which further comprises applying the negative pressure in the interior of the sleeve at less than or equal to 0.6 bar.

24. The process according to claim 1, which further comprises applying the negative pressure in the interior of the sleeve in a range from 0.01 bar to 0.6 bar.

25. The process according to claim 1, which further comprises applying the negative pressure in the interior of the sleeve in a range from 0.1 bar to 0.6 bar.

26. The process according to claim 1, which further comprises applying the negative pressure in the interior of the sleeve in a range from 0.3 bar to 0.6 bar.

27. A configuration, comprising:
   a sleeve having an interior;
   an implant having a supporting structure with a multiplicity of through openings; and
   a balloon having an interior, said balloon being disposed in said interior of said sleeve and crimped to said implant, said balloon being deep-drawn into said through openings of said implant and fixed by a form-locking connection between said balloon and said supporting structure of said implant by a negative pressure applied to said interior of said sleeve and a positive pressure applied to said interior of said balloon.

28. An apparatus for fixing an implant to a balloon, the apparatus comprising:
   a balloon having interior;
   an implant crimped to said balloon;
   a sleeve having an interior for receiving said implant crimped to said balloon;
   a pump to be brought into flow connection with said interior of said sleeve and configured to produce a negative pressure in said interior of said sleeve;
   a device to be brought into flow connection with said interior of said balloon and configured to apply a positive pressure to said interior of said balloon while said negative pressure is produced in said interior of said sleeve; and
   a heating device configured to heat said balloon.

29. The apparatus according to claim 28, which further comprises a tube configured to surround said implant disposed in said interior of said sleeve, said implant being disposed between said balloon and said tube.

30. The apparatus according to claim 28, wherein said tube includes a circumferential wall having at least one or a multiplicity of openings formed in said circumferential wall.

* * * * *